US009625436B2

(12) United States Patent
Mazurkiewicz et al.

(10) Patent No.: US 9,625,436 B2
(45) Date of Patent: Apr. 18, 2017

(54) DETERMINING THE GEOGRAPHIC ORIGIN OF METALS

(71) Applicant: Hewlett-Packard Development Company, L.P., Fort Collins, CO (US)

(72) Inventors: Paul Howard Mazurkiewicz, Fort Collins, CO (US); Paul Hubbard Ford, Fort Collins, CO (US); Troy A. Farrar, Omaha, NE (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 785 days.

(21) Appl. No.: 13/872,987

(22) Filed: Apr. 29, 2013

(65) Prior Publication Data

US 2014/0324347 A1    Oct. 30, 2014

(51) Int. Cl.
*G01V 1/00*      (2006.01)
*G01N 33/20*     (2006.01)

(52) U.S. Cl.
CPC ................... *G01N 33/20* (2013.01)

(58) Field of Classification Search
CPC .......... Y10T 436/24; G01N 2030/8868; G01N 33/20; G06F 17/40; G06F 19/00; H01J 49/0036; B01D 59/44
See application file for complete search history.

(56) References Cited

U.S. PATENT DOCUMENTS 7,301,150 B2   11/2007   Hailey
8,367,414 B2    2/2013   Jasper 2009/0042304 A1 *  2/2009  Anderson ............. G01N 33/02
                                                   436/20
2010/0295699 A1   11/2010  Rushing
2012/0123582 A1 *  5/2012  Jasper ................... G01N 33/15
                                                  700/107

OTHER PUBLICATIONS

Melcher et al., Analytical fingerprint (AFP) for tantalum ("coltan"), tin, and tungsten ores, AFP Update Jul. 2010.
Bauwens, Conflict Minerals Traceability: A Scientific Proof, MJB Consulting African Business & Legal Intelligence, Jul. 27, 2011.
Melcher et al., Fingerprinting of conflict minerals: columbite-tantalite ("coltan") ores, Society for Geology Applied to Mineral Deposits, Jun. 2008, No. 23.
Arnaud, Fingerprinting Conflict Minerals, Chemical & Engineering News, Apr. 30, 2012, vol. 90 Issue 18, pp. 36-37.
Geochemical Fingerprinting of Conflict Minerals using LIBS, Applied Spectra A Laser Solutions Company.
Shughrue et al., Provenance Determination of Conflict Minerals by Laser-Induced Breakdown Spectroscopy: The Example of Columbite-Tantalite, 2010 GSA Denver Annual Meeting (Oct. 31-Nov. 3, 2010), Paper No. 132-9.

* cited by examiner

*Primary Examiner* — Elias Desta
(74) *Attorney, Agent, or Firm* — Thorpe, North & Western L.L.P.

(57) ABSTRACT

A method of determining the geographic origin of a metal can comprise measuring a first isotope and a second isotope of the metal by high-resolution mass spectrometry; calculating a ratio of the first isotope and the second isotope; comparing the ratio to native ratios of isotopes of the metal of native samples from a plurality of geographic locations using a database; and matching the ratio to a geographic location.

20 Claims, 2 Drawing Sheets

DETERMINING THE GEOGRAPHIC ORIGIN OF METALS

BACKGROUND

The desirability of using non-conflict materials has been recognized in various industries for public interest reasons. With the passage of Dodd-Frank Wall Street Reform and Consumer Protection Act in the United States, companies can now be required to monitor the origin of specific metals that can be mined from regions experiencing serious civil unrest. In these areas, the money from the mines may be used to pay for atrocities and to fuel wars led by armed militias. Currently, due-diligence methods include the use of paper trails, which suffer from issues such as forgery, bribery and mismanagement. Other methods include analytical methods that can identify the source of ores, but once the ores are processed, these methods cannot reveal the origin of the metals.

BRIEF DESCRIPTION OF THE DRAWINGS

Additional features and advantages of the disclosure will be apparent from the detailed description which follows, taken in conjunction with the accompanying drawings, which together illustrate, by way of example, features of the invention, and wherein.

Figure 1:
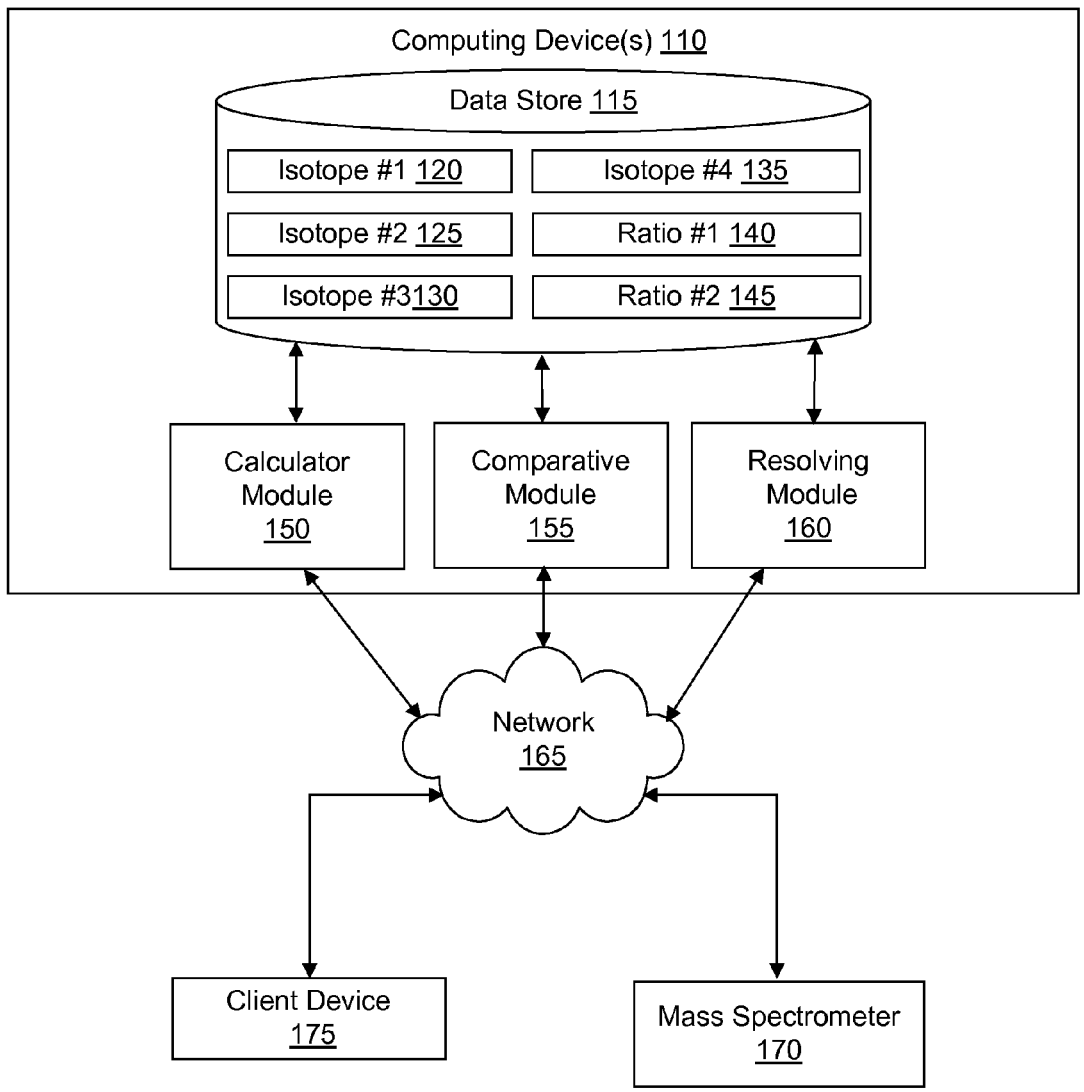
FIG. 1 is a block diagram illustrating a networked computer system usable for determining the origin of a metal in accordance with an example of the present disclosure.

Reference will now be made to the exemplary embodiments illustrated, and specific language will be used herein to describe the same. It will nevertheless be understood that no limitation of the scope of the invention is thereby intended.

DETAILED DESCRIPTION

Before the present disclosure is described herein, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Reference will now be made to the exemplary embodiments illustrated, and specific language will be used herein to describe the same. It will nevertheless be understood that no limitation of the scope of the technology is thereby intended. Additional features and advantages of the technology will be apparent from the detailed description which follows, taken in conjunction with the accompanying drawings, together illustrating, by way of example, features of the technology.

The present disclosure provides a method for determining the origin of metals in a finished product that is independent of due diligence protocols including chain-of-custody paperwork and can be used on post processed metals. Notably, as previously discussed, other methods that attempt to determine the origin of a metal measure impurities in an ore sample and match the impurity levels to known geographical samples. However, such methods will not work on processed ore as those impurities are removed or can be drastically altered. As such, the present method is particularly advantageous as it is based on isotope ratios of the metal per se, which remain unchanged during and subsequent to processing.

As discussed herein, the present disclosure provides methods and apparatuses for determining the geographical location of a metal using isotope ratios. As such, the present disclosure is based on fundamental properties of the chemical elements. Every chemical element has a specific number of protons that determines the identity of that particular element. For example, carbon has 6 protons. If another proton is added, this element would become nitrogen with 7 protons. However, there is another fundamental particle present in the nuclei of elements, i.e. the neutron. The number of neutrons in a chemical element can vary. A chemical element with a different number of neutrons is called an isotope of that element. As an example, the chemical element tin has ten different stable isotopes. The tin mined from the ground is normally a mixture of these isotopes. By using ratios of the isotopes of a metal found in a particular sample, the geographical location or region of the metal can be determined. Based on this fundamental characteristic, ratios can be measured from processed metals to determine the origin of the metal.

In light of the above, a method of determining the geographic origin of a metal in a sample can comprise measuring a first isotope and a second isotope of the metal by high-resolution mass spectrometry, calculating a ratio of the first isotope and the second isotope, comparing the ratio to native ratios of isotopes of the metal of native samples from a plurality of geographic locations using a database, and matching the ratio to a geographic location.

In another example, an apparatus for determining the geographic origin of a metal in a sample can comprise a high-resolution mass spectrometer, a calculator module, a database, and a comparative module. The high-resolution mass spectrometer can be configured to measure a first isotope and a second isotope of the metal. The calculator module can be operably connected to the high-resolution mass spectrometer, and can be configured to calculate a ratio of the first isotope and the second isotope. The database can include native ratios of isotopes of the metal from a plurality of geographic locations. The comparative module can be operably connected to the calculator module and the database, and can be configured to match the ratio to one of the native ratios and assign a geographical location to the metal.

It is noted that when discussing the present methods and apparatuses, each of these discussions can be considered applicable to each of these embodiments, whether or not they are explicitly discussed in the context of that embodiment. Thus, for example, in discussing a high-resolution mass spectrometer in a method for determining the origin of a metal, such a high-resolution mass spectrometer can also be used in an apparatus for determining the geographic origin of a metal, and vice versa.

The present methods and apparatuses can be applicable to any metal having isotopes. In one aspect, the isotope can be a stable isotope. In another aspect, the isotope can be radioactive. In one example, the isotopes of the ratio can be both stable isotopes. Alternately, the ratio can use a mixture of stable and radioactive isotopes. In one example, the metal can be a metal typically mined from a conflict region of interest. In one aspect, the region can be Democratic Republic of the Congo. In one example, the metal can include tin, tantalum, tungsten, gold, mixtures thereof, and alloys thereof. Additionally, the metal can include alloys using the metal. In one aspect, the metal can be tin. In another aspect, the metal can be tungsten. In yet another aspect, the metal can be gold. In still another aspect, the metal can be tantalum.

The present ratio can be chosen to match a distinct ratio of the metal. As such, the ratio can be from any two isotopes of the metal where the ratio provides differentiation between geographical locations or regions. For example, if the metal of interest has a common isotope and a rare (least common) isotope and the ratio of such isotopes is distinct from region to region or location to location, such a ratio may serve as a unique identifier and be used to determine the origin of a metal. Additionally, more than one ratio may be used. In one example, the method can further comprise measuring a third isotope and a fourth isotope, calculating a second ratio of two isotopes selected from the group consisting of the first isotope, the second isotope, the third isotope, and the fourth isotope, with the proviso that one or two isotopes of the second ratio includes the third isotope or the fourth isotope, and comparing the second ratio to native ratios. Such a method can extend to any number of isotopes present for the metal, e.g., a fifth isotope, a sixth isotope, a seventh isotope, etc. The method can include additional ratios from such isotopes such that a unique fingerprint is created sufficient to differentiate regions or locations as desired.

Further, the present methods and apparatuses can be used to resolve a mixture of metals in a given sample from differing geographical locations or regions by using selected ratios from each metal. As discussed herein, by using a set of ratios for each metal, a unique fingerprint can be assigned to differing metals. This unique fingerprint can be used to differentiate a mixture of metals in a given sample.

The present isotopes can be measured by any instrument capable of such measurements. In one example, the instrument can be a high-resolution mass spectrometer.

The present methods and apparatuses can further comprise a database that is created and used to store ratios from samples collected from various geographical regions or locations. As such, native samples of the metal from the geographic locations can be obtained, and first isotopes and second isotopes of the metal from the native samples can be measured by high-resolution mass spectrometry. The native ratios from the first isotopes and the second isotopes can be calculated these native ratios can be stored for future comparison purposes as they relate to an individual geographic location.

As discussed herein, the high-resolution mass spectrometer can be configured to measure a third isotope and a fourth isotope and the calculator module is configured to calculate a second ratio of at least two isotopes selected from the group consisting of the first isotope, the second isotope, the third isotope, and the fourth isotope, with the proviso that one or two isotopes of the second ratio includes the third isotope or the fourth isotope.

Turning now to FIG. 1, the apparatus can comprise various individual components commonly networked. The networked environment may include one or more computing devices 110 in data communication with a high-resolution mass spectrometer 170 by way of a network 165. The network may include the Internet, intranets, extranets, wide area networks (WANs), local area networks (LANs), wired networks, wireless networks, or other suitable networks, etc., or any combination of two or more such networks.

The computing device 110 may comprise, for example, a server computer or any other system providing computing capability. Alternatively, a plurality of computing devices may be employed that are arranged, for example, in one or more server banks, computer banks, or other computing arrangements. Such computing devices may be located in a single installation or may be distributed among many different geographical locations. For purposes of convenience, the computing device is referred to herein in the singular. Even though the computing device is referred to in the singular, it is understood that a plurality of computing devices may be employed in the various arrangements as described above.

The client device 175 is representative of a plurality of client devices that may be coupled to the network 165. The client device may comprise, for example, a processor-based system such as a computer system. Such a computer system may be embodied in the form of a desktop computer, a laptop computer, or other devices with like capability.

The isotope and native ratio data may be stored in a data store 115 that is accessible to the computing device. The term "data store" may refer to any device or combination of devices capable of storing, accessing, organizing, and/or retrieving data, which may include any combination and number of data servers, relational databases, object oriented databases, simple web storage systems, cloud storage systems, data storage devices, data warehouses, flat files, and data storage configuration in any centralized, distributed, or clustered environment. The storage system components of the data store may include storage systems such as a SAN (Storage Area Network), cloud storage network, volatile or non-volatile RAM, optical media, or hard-drive type media. The data stored in the data store 115, for example, may be associated with the operation of the various applications and/or functional entities described below.

The data stored in the data store 115 may include a first isotope 120 (isotope #1), a second isotope 125 (isotope #2), a third isotope 130 (isotope #3), a fourth isotope 135 (isotope #4), a first ratio 140 (ratio #1), a second ratio 145 (ratio #2), and/or the like. A calculator module 150 can transform the native isotopes into native ratios and store such native ratios in the data store thereby creating a library of native ratios, each of which are specific to a geographical location or region. Additionally, the calculator module can receive isotope measurements from metal samples from the high-resolution mass spectrometer 170 and calculate ratios and store them in the data store. Once the metal sample ratio has been calculated, the comparative module 155 can index the metal isotope ratio to a native ratio and determine the geographic origin of the metal. Additionally, if more than one metal is present, a resolving module 160 can resolve two different metals from a sample using a set of ratios for each metal. The resolving module can be configured to resolve a first metal from a second metal in the sample by identifying a unique fingerprint for the first metal and the second metal, the unique fingerprint of the first metal corresponding to a set of ratios that distinguishes the first metal from the second metal and the unique fingerprint of the second metal corresponding to a set of ratios that distinguishes the second metal from the first metal.

Certain processing modules may be discussed in connection with this technology and FIG. 1. In one example configuration, a module may be considered a service with one or more processes executing on a server or other computer hardware. Such services may be centrally hosted functionality or a service application that may receive requests and provide output to other services or consumer devices. For example, modules providing services may be considered on-demand computing that is hosted in a server, cloud, grid, or cluster computing system. An application program interface (API) may be provided for each module to enable a second module to send requests to and receive output from the first module. Such APIs may also allow third parties to interface with the module and make requests and receive output from the modules. In one example, a third party can access the modules using authentication credentials that provide on-going access to the module.

Figure 2:
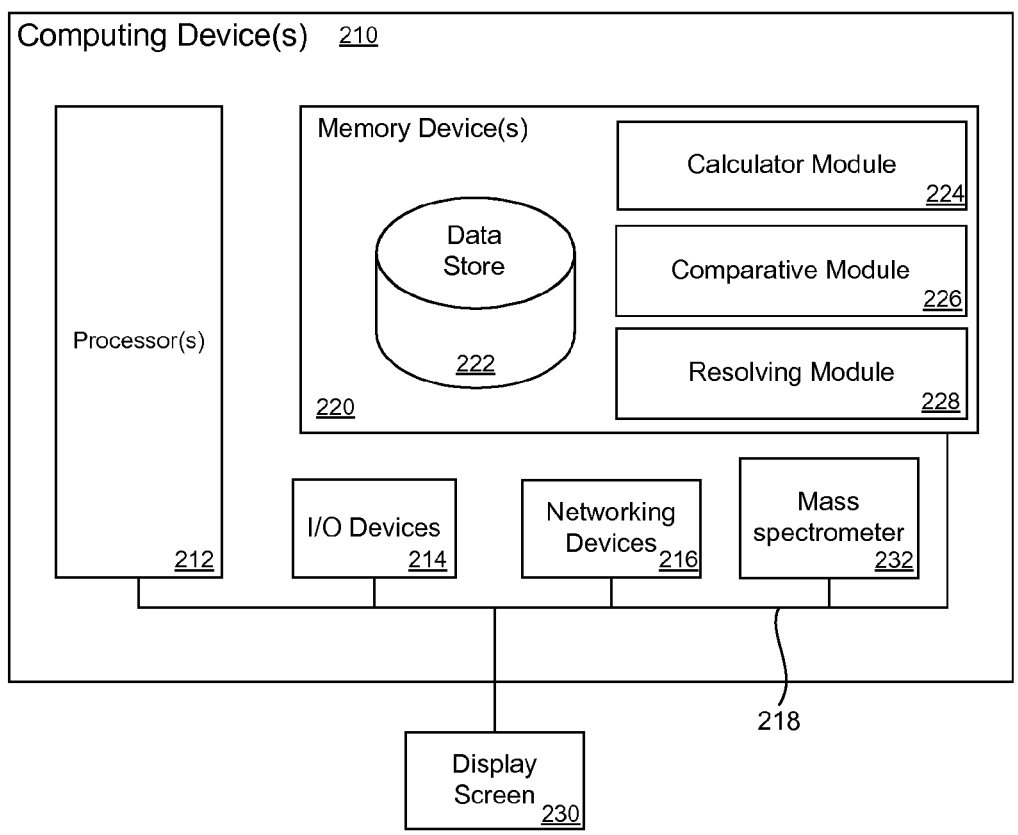
FIG. 2 is a block diagram illustrating a device usable for determining the origin of a metal in accordance with an example of the present disclosure.

FIG. 2 illustrates a computing device 210 on which modules of this technology may execute. More specifically, a computing device is illustrated on which a high level example of the technology may be executed. The computing device may include one or more processors 212 that are in communication with memory devices 220. The computing device may include a local communication interface 218 for the components in the computing device. For example, the local communication interface may be a local data bus and/or any related address or control busses as may be desired.

The memory device 220 may contain modules that are executable by the processor(s) 212 and data for the modules. Located in the memory device are modules executable by the processor. For example, a calculator module 224 and a comparative module 226, a resolving module 228, and other modules may be located in the memory device. The modules may execute the functions described earlier. A data store 222 may also be located in the memory device for storing data related to the modules and other applications along with an operating system that is executable by the processor(s).

Other applications may also be stored in the memory device 220 and may be executable by the processor(s) 212. Components or modules discussed in this description may be implemented in the form of software using high programming level languages that are compiled, interpreted or executed using a hybrid of the methods.

The computing device may also have access to I/O (input/output) devices 214 that are usable by the computing devices. An example of an I/O device is a display screen 230 that is available to display output from the computing devices. Other known I/O device may be used with the computing device as desired. Networking devices 216 and similar communication devices may be included in the computing device. Further, a high-resolution mass spectrometer 232 can be directly connected to the networking device 216. The networking devices 216 may be wired or wireless networking devices that connect to the internet, a LAN, WAN, or other computing network.

The components or modules that are shown as being stored in the memory device 220 may be executed by the processor 212. The term "executable" may mean a program file that is in a form that may be executed by a processor. For example, a program in a higher level language may be compiled into machine code in a format that may be loaded into a random access portion of the memory device and executed by the processor, or source code may be loaded by another executable program and interpreted to generate instructions in a random access portion of the memory to be executed by a processor. The executable program may be stored in any portion or component of the memory device. For example, the memory device may be random access memory (RAM), read only memory (ROM), flash memory, a solid state drive, memory card, a hard drive, optical disk, floppy disk, magnetic tape, or any other memory components.

The processor 212 may represent multiple processors and the memory 220 may represent multiple memory units that operate in parallel to the processing circuits. This may provide parallel processing channels for the processes and data in the system. The local interface 218 may be used as a network to facilitate communication between any of the multiple processors and multiple memories. The local interface may use additional systems designed for coordinating communication such as load balancing, bulk data transfer, and similar systems.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here can also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which can be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

The following terminology will be used in accordance with the definitions set forth below.

As used herein, the singular forms "a," and, "the" include plural referents unless the context clearly dictates otherwise.

As used herein, the term "alloy" refers to any mixture or metallic solid solution composed of two or more elements. Alloys can be classified as substitutional or interstitial alloys, depending on the atomic arrangement that forms the alloy, both of which are included in the present term unless otherwise specified. Additionally, such alloys can be further classified as homogeneous (consisting of a single phase), or heterogeneous (consisting of two or more phases) or intermetallic (where there is no distinct boundary between phases). The present term includes all such types of alloys unless otherwise specified. Additionally, in certain examples, an alloy can be a substitutional alloy, an interstitial alloy, a homogenous alloy, a heterogeneous alloy, and/or a intermetallic alloy.

As used herein, the term "substantially" refers to the complete or nearly complete extent or degree of an action, characteristic, property, state, structure, item, or result. The exact allowable degree of deviation from absolute completeness may in some cases depend on the specific context. However, generally speaking, the nearness of completion will be so as to have the same overall result as if absolute and total completion were obtained.

As used herein, the term "about" is used to provide flexibility to a numerical range endpoint by providing that a given value may be "a little above" or "a little below" the endpoint.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. Additionally, a numerical range with a lower end of "0" can include a sub-range using "0.1" as the lower end point.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

In some examples, specific sizes, shapes, dimensions, etc. may be provided for illustrative purposes. However, such examples are intended to be non-limiting and a variety of other sizes, shapes, dimensions, etc. may be implemented to accommodate specific applications. These specific dimensions are not to be construed as critical to the invention, and in fact, may be modified liberally for other specific configurations.

EXAMPLES

The following examples illustrate some examples of the present methods and apparatuses that are presently known. However, it is to be understood that the following are only illustrative of the application of the principles of the present methods and apparatuses. Numerous modifications and alternative methods and apparatuses may be devised by those skilled in the art without departing from the spirit and scope of the present methods and apparatuses. The appended claims are intended to cover such modifications and arrangements. Thus, while the present methods and apparatuses have been described above with particularity, the following examples provide further detail in connection with what are presently deemed to be the acceptable embodiments.

Example 1

Determining the Origin of Tin

Tin has 10 stable isotopes as listed in Table 1. Samples of tin are obtained from 4 geographical locations and analyzed with a high-resolution mass spectrometer to obtain the isotopic amounts listed in Table 2.

TABLE 1

| Tin Isotope | Isotope Natural abundance (atom %) | Isotopic enrichment (atom %) |
|---|---|---|
| 112 | 0.96 | 68-80 |
| 114 | 0.66 | >61 |
| 115 | 0.35 | >32 |
| 116 | 14.30 | >95 |
| 117 | 7.61 | >89 |
| 118 | 24.03 | >97 |
| 119 | 8.58 | >84 |
| 120 | 32.85 | >98 |

TABLE 1-continued

| Tin Isotope | Isotope Natural abundance (atom %) | Isotopic enrichment (atom %) |
|---|---|---|
| 122 | 4.72 | >92 |
| 124 | 5.94 | >94 |

TABLE 2

| Isotope | Geographic Location A (% isotope) | Geographic Location B (% isotope) | Geographic Location C (% isotope) | Geographic Location D (% isotope) |
|---|---|---|---|---|
| 112 | 0.90 | 0.90 | 0.95 | 0.92 |
| 114 | 0.60 | 0.65 | 0.65 | 0.62 |
| 115 | 0.35 | 0.33 | 0.32 | 0.34 |
| 116 | 14.0 | 15.3 | 14.5 | 14.9 |
| 117 | 7.6 | 7.5 | 7.5 | 7.0 |
| 118 | 25.3 | 25 | 24 | 24.3 |
| 119 | 8.3 | 8.6 | 8.5 | 8.55 |
| 120 | 32.45 | 30.52 | 33.6 | 32.72 |
| 122 | 4.5 | 4.7 | 4.48 | 4.75 |
| 124 | 6 | 6.5 | 5.5 | 5.9 |

Native ratios are calculated for the geographical location as listed in Table 3.

TABLE 3

| Isotope Ratio | Geographic Location A | Geographic Location B | Geographic Location C | Geographic Location D |
|---|---|---|---|---|
| 120:112 | 36.06 | 33.91 | 35.37 | 35.57 |
| 120:118 | 1.28 | 1.22 | 1.4 | 1.35 |
| 115:112 | 0.39 | 0.37 | 0.34 | 0.37 |
| 118:119 | 3.05 | 2.91 | 2.82 | 2.84 |

Once the library of native ratios is calculated and stored, an unknown sample of tin can be obtained and analyzed. Once the isotopes are determined for the sample, ratios can be calculated and compared against the stored native ratios to determine the origin of the sample. As can be seen in Table 3, not every ratio may be unique. As such, multiple ratios can be used as would be useful to create a unique identifier that distinguishes each native sample.

What is claimed is:

1. A method of determining the geographic origin of a sample including an elemental metal with an apparatus including high resolution mass spectrometer device, comprising:
   measuring, using the high resolution mass spectrometer device of the apparatus, a first isotope and a second isotope of the elemental metal;
   calculating, using a processor of the apparatus, a ratio of the first isotope to the second isotope of the elemental metal measured by the high resolution mass spectrometer device;
   comparing, using the processor of the apparatus, the ratio to native ratios of two isotopes of the elemental metal of native samples from a plurality of geographic locations using a database of the apparatus; and
   matching, using the processor of the apparatus, the ratio to a geographic location,
   wherein the ratio of the first isotope and the second isotope that is calculated and compared to the native ratios is of isotopes of a same elemental metal.

2. The method of claim 1, wherein the elemental metal is tantalum or gold.

3. The method of claim 1, wherein the elemental metal is tin.

4. The method of claim 1, wherein the elemental metal is tungsten.

5. The method of claim 1, wherein one of the first isotope and the second isotope is a stable isotope.

6. The method of claim 1, wherein both the first isotope and the second isotope are stable isotopes.

7. The method of claim 1, further comprising:
   measuring, using the high resolution mass spectrometry, a third isotope and a fourth isotope;
   calculating, using the processor, a second ratio of two isotopes selected from the group consisting of the first isotope, the second isotope, the third isotope, and the fourth isotope, with the proviso that one or two isotopes of the second ratio includes the third isotope or the fourth isotope; and
   comparing, using the processor, the second ratio to the native ratios.

8. The method of claim 7, wherein one of the third isotope and the fourth isotope is a stable isotope.

9. The method of claim 7, wherein both the third isotope and the fourth isotope are stable isotopes.

10. The method of claim 1, further comprising creating the database by:
    obtaining native samples including the elemental metal from the geographic locations;
    measuring, using high resolution mass spectrometry, first isotopes and second isotopes of the elemental metal from the native samples;
    calculating, using the processor, the native ratios from the first isotopes and the second isotopes; and
    storing, using the processor, the native ratios from the native samples in the database where each native ratio corresponds to an individual geographic location.

11. The method of claim 1, further comprising:
    measuring, using the high resolution mass spectrometry, a first isotope and a second isotope of a second elemental metal in the sample;
    calculating, using the processor, a second metal ratio of the first isotope and the second isotope, wherein the second metal ratio is distinguishable over the ratio of the elemental metal;
    comparing, using the processor, the second metal ratio to native ratios of isotopes of the second elemental metal of native samples from a plurality of geographic locations using a database; and
    matching, using the processor, the second metal ratio to a geographic location.

12. An apparatus for determining the geographic origin of a sample including an element metal with a high resolution mass spectrometer device, comprising:
    a high-resolution mass spectrometer device configured to measure a first isotope and a second isotope of the elemental metal;
    a calculator module operably connected to the high-resolution mass spectrometer device, the calculator module configured to calculate a ratio of the first isotope to the second isotope of the elemental metal measured by the high-resolution mass spectrometer device;
    a database, the database comprising native ratios of two isotopes of the elemental metal from a plurality of geographic locations; and a comparative module operably connected to the calculator module and the database, the comparative module configured to match the ratio to one of the native ratios and assign a geographical location to the sample including the elemental metal, wherein the ratio of the first isotope and the second isotope that is calculated and compared to the native ratios is of isotopes of a same elemental metal.

13. The apparatus of claim 12, wherein the elemental metal is selected from the group consisting of tin, tantalum, tungsten, and gold.

14. The apparatus of claim 12, wherein the high-resolution mass spectrometer is configured to measure a third isotope and a fourth isotope and the calculator module is configured to calculate a second ratio of at least two isotopes selected from the group consisting of the first isotope, the second isotope, the third isotope, and the fourth isotope, with the proviso that one or two isotopes of the second ratio includes the third isotope or the fourth isotope.

15. The apparatus of claim 12, further comprising a resolving module operably connected to the calculator module, the comparative module, and the database, the resolving module configured to resolve the elemental metal from a second elemental metal in the sample by identifying a unique fingerprint for the elemental metal and the second elemental metal, the unique fingerprint of the elemental metal corresponding to a set of ratios that distinguishes the elemental metal from the second elemental metal and the unique fingerprint of the second elemental metal corresponding to a set of ratios that distinguishes the second elemental metal from the elemental metal.

16. The method of claim 1, wherein the sample is a processed ore including the elemental metal.

17. The method of claim 1, wherein the sample consists essentially of the elemental metal.

18. The method of claim 1, wherein the sample is an alloy of the elemental metal.

19. The apparatus of claim 12, wherein the sample is a processed ore of the elemental metal.

20. The apparatus of claim 12, wherein the sample consists of the elemental metal.

* * * * *